(12) United States Patent
Wong et al.

(10) Patent No.: US 7,588,895 B2
(45) Date of Patent: Sep. 15, 2009

(54) BIOMARKERS FOR ORAL TONGUE CANCER METASTASIS AND EXTRACAPSULAR SPREAD (ECS)

(75) Inventors: David T. W. Wong, Beverly Hills, CA (US); Xiaofeng Zhou, Chicago, IL (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/622,061

(22) Filed: Jan. 11, 2007

(65) Prior Publication Data

US 2007/0207479 A1    Sep. 6, 2007

Related U.S. Application Data

(60) Provisional application No. 60/758,432, filed on Jan. 11, 2006.

(51) Int. Cl.
*C12Q 1/68* (2006.01)
(52) U.S. Cl. .......................................................... 435/6
(58) Field of Classification Search ...................... 435/6
See application file for complete search history.

(56) References Cited

U.S. PATENT DOCUMENTS 6,063,586 A    5/2000   Grandis

OTHER PUBLICATIONS

Tockman et al (Cancer Res., 1992, 52:2711s-2718s).*
Bringuier et al (Oncogene, Apr. 1996, 12:1747-1753).*
Rodrigo et al (Clinical Cancer Research, Aug. 2000, 6:3177-3182).*
Hui et al (Oncogene, 1998, 17: 1053-1059).*
Hardiman (Parmacogenomics, 2004, 5(5): 487-502).*
Westin et al (Mediators of Inflammation, 2002, 11: 7-12).*
Masuda, Masuda et al.; "Effects of Epigallocatechin-3-gallate on Growth, Epidermal Growth Factor Receptor Signaling Pathways, Gene Expression, and Chemosensitivity in Human Head and Neck Squamous Cell Carcinoma Cell Lines"; 2001, *Clinical Cancer Research*, vol. 7, pp. 4220-4229.
Riedel, F. et al.; "Expression of 92-kDa type IV collagenase correlates with angiogenic markers and poor survival in head and neck squamous cell carcinoma"; 2000, *Int. J. Oncol.*, vol. 17, No. 6, 1 page abstract.
Villaret, Douglas B. et al.; "Identification of Genes Overexpressed in Head and Neck Squamous Cell Carcinoma Using a Combination of Complementary DNA Subtraction and Microarray Analysis"; 2000, *Laryngoscope*, vol. 110, No. 3, 1 page abstract.

* cited by examiner

*Primary Examiner*—Sean E Aeder
(74) *Attorney, Agent, or Firm*—Townsend and Townsend and Crew LLP (57) ABSTRACT

The present invention provides for the first time molecular diagnostic and prognostic markers for tongue cancer metastasis and extracapsular spread that are independent of histopathological evaluation.

12 Claims, 2 Drawing Sheets

A 36 probes representing 33 genes     25 probes representing 22 genes

B

|  | pN- * | pN+ * |  |  | ECS- * | ECS+ * |  |  |
|---|---|---|---|---|---|---|---|---|
|  |  |  | wilcoxon | ttest |  |  | wilcoxon | ttest |
| BMP2 | 7.99 | 15.81 | .043 | .458 | 7.37 | 21.97 | .069 | .208 |
| CTTN | 2.41 | 14.85 | <.0001 | .013 | 3.60 | 18.71 | .004 | .006 |
| EEF1A1 | 0.81 | 0.32 | .078 | .044 | 0.73 | 0.28 | .064 | .103 |
| ASAH1 | 1.40 | 1.00 | .259 | .513 | 1.42 | 0.71 | .209 | .303 |
| MTUS1 | 1.26 | 0.88 | .364 | .486 | 1.15 | 0.97 | .544 | .765 |
| GTSE1 | 2.05 | 6.90 | .013 | .067 | 2.64 | 8.09 | .107 | .064 |
| MMP9 | 2.59 | 33.81 | .001 | .083 | 3.37 | 49.55 | .001 | .018 |
| EGFR | 1.63 | 5.20 | .004 | .045 | 2.03 | 6.14 | .055 | .038 |

Figure 3

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence -continued

```
<220> FEATURE:
<223> OTHER INFORMATION: bone morphogenetic protein 2 (BMP2) real-time
      quantitative PCR (RT-PCR) left primer

<400> SEQUENCE: 1
aactctcctc ctgcccctta                                                      20

<210> SEQ ID NO 2
<211> LENGTH: 20
<212> TYPE: DNA
<213> ORGANISM: Artificial Sequence
<220> FEATURE:
<223> OTHER INFORMATION: bone morphogenetic protein 2 (BMP2) real-time
      quantitative PCR (RT-PCR) right primer

<400> SEQUENCE: 2
tgcaggttca tcgttttcct                                                      20

<210> SEQ ID NO 3
<211> LENGTH: 20
<212> TYPE: DNA
<213> ORGANISM: Artificial Sequence
<220> FEATURE:
<223> OTHER INFORMATION: eukaryotic translation elongation factor 1
      alpha1-like 14 (EEF1A1L14; prostate tumor-inducing gene
      (PTI1)) real-time quantitative PCR (RT-PCR) left primer

<400> SEQUENCE: 3
agtctggtga tgctgccatt                                                      20

<210> SEQ ID NO 4
<211> LENGTH: 20
<212> TYPE: DNA
<213> ORGANISM: Artificial Sequence
<220> FEATURE:
<223> OTHER INFORMATION: eukaryotic translation elongation factor 1
      alpha1-like 14 (EEF1A1L14; prostate tumor-inducing gene
      (PTI1)) real-time quantitative PCR (RT-PCR) rightprimer

<400> SEQUENCE: 4
gcgacccaaa ggtggatagt                                                      20

<210> SEQ ID NO 5
<211> LENGTH: 21
<212> TYPE: DNA
<213> ORGANISM: Artificial Sequence
<220> FEATURE:
<223> OTHER INFORMATION: cortactin (CTTN; oncogene EMS1) real-time
      quantitative PCR (RT-PCR) left primer

<400> SEQUENCE: 5
ctgagttctt ccttccccac t                                                    21

<210> SEQ ID NO 6
<211> LENGTH: 21
<212> TYPE: DNA
<213> ORGANISM: Artificial Sequence
<220> FEATURE:
<223> OTHER INFORMATION: cortactin (CTTN; oncogene EMS1) real-time
      quantitative PCR (RT-PCR) right primer

<400> SEQUENCE: 6
taaatgtgca ggccaaacaa g                                                    21

<210> SEQ ID NO 7
<211> LENGTH: 21
<212> TYPE: DNA
```

```
<213> ORGANISM: Artificial Sequence
<220> FEATURE:
<223> OTHER INFORMATION: G-2 and S-phase expressed 1 (GTSE1; B99)
      real-timequantitative PCR (RT-PCR) left primer

<400> SEQUENCE: 7
gttctaagcc gaaccaaatc c                                          21

<210> SEQ ID NO 8
<211> LENGTH: 21
<212> TYPE: DNA
<213> ORGANISM: Artificial Sequence
<220> FEATURE:
<223> OTHER INFORMATION: G-2 and S-phase expressed 1 (GTSE1; B99)
      real-timequantitative PCR (RT-PCR) right primer

<400> SEQUENCE: 8
acctcagcct cccaagttct a                                          21

<210> SEQ ID NO 9
<211> LENGTH: 20
<212> TYPE: DNA
<213> ORGANISM: Artificial Sequence
<220> FEATURE:
223> OTHER INFORMATION: N-acylsphingosine amidohydrolase (acid
      ceramidase) 1 (ASAH1; acylsphingosine deacylase (AC), PHP32)
      real-time quantitative PCR (RT-PCR) left primer

<400> SEQUENCE: 9
ttgcctcttc gtgaactttg                                            20

<210> SEQ ID NO 10
<211> LENGTH: 20
<212> TYPE: DNA
<213> ORGANISM: Artificial Sequence
<220> FEATURE:
<223> OTHER INFORMATION: N-acylsphingosine amidohydrolase (acid
      ceramidase) 1 (ASAH1; acylsphingosine deacylase (AC), PHP32)
      real-time quantitative PCR (RT-PCR) right primer

<400> SEQUENCE: 10
accacccaaa taccctgttg                                            20

<210> SEQ ID NO 11
<211> LENGTH: 20
<212> TYPE: DNA
<213> ORGANISM: Artificial Sequence
<220> FEATURE:
<223> OTHER INFORMATION: matrix metalloproteinase 9 (MMP9 (gelatinase
      B (GELB), 92kD gelatinase, 92kD type IV collagenase), type
      V collagenase, macrophage gelatinase; CLE4B) real-time
      quantitative PCR (RT-PCR) left primer

<400> SEQUENCE: 11
gcacgacgtc ttccagtacc                                            20

<210> SEQ ID NO 12
<211> LENGTH: 20
<212> TYPE: DNA
<213> ORGANISM: Artificial Sequence
<220> FEATURE:
<223> OTHER INFORMATION: matrix metalloproteinase 9 (MMP9 (gelatinase
      B (GELB), 92kD gelatinase, 92kD type IV collagenase), type
      V collagenase, macrophage gelatinase; CLE4B) real-time
      quantitative PCR (RT-PCR) right primer

<400> SEQUENCE: 12
tcaactcact ccgggaactc                                            20
```

```
<210> SEQ ID NO 13
<211> LENGTH: 20
<212> TYPE: DNA
<213> ORGANISM: Artificial Sequence
<220> FEATURE:
<223> OTHER INFORMATION: epidermal growth factor receptor (EGFR; avian
      erythroblastic leukemia viral (v-erb-b) oncogene homolog (ERBB);
      mENA; cell growth inhibiting protein 40) real-time quantitative
      PCR (RT-PCR) left primer

<400> SEQUENCE: 13
gcatctttaa gggctccaca                                                    20

<210> SEQ ID NO 14
<211> LENGTH: 20
<212> TYPE: DNA
<213> ORGANISM: Artificial Sequence
<220> FEATURE:
<223> OTHER INFORMATION: epidermal growth factor receptor (EGFR; avian
      erythroblastic leukemia viral (v-erb-b) oncogene homolog (ERBB);
      mENA; cell growth inhibiting protein 40) real-time quantitative
      PCR (RT-PCR) right primer

<400> SEQUENCE: 14
actatcctcc gtggtcatgc                                                    20

<210> SEQ ID NO 15
<211> LENGTH: 20
<212> TYPE: DNA
<213> ORGANISM: Artificial Sequence
<220> FEATURE:
<223> OTHER INFORMATION: mitochondrial tumor suppressor 1 (MTUS1; AT2
      receptor-interacting protein (ATIP); erythroid
      differentiation-related; MP44; MTSG1 transcription
      factor) real-time quantitative PCR (RT-PCR) left primer

<400> SEQUENCE: 15
tatctctgct cacgcttcca                                                    20

<210> SEQ ID NO 16
<211> LENGTH: 20
<212> TYPE: DNA
<213> ORGANISM: Artificial Sequence
<220> FEATURE:
<223> OTHER INFORMATION: mitochondrial tumor suppressor 1 (MTUS1; AT2
      receptor-interacting protein (ATIP); erythroid
      differentiation-related; MP44; MTSG1 transcription
      factor) real-time quantitative PCR (RT-PCR) right primer

<400> SEQUENCE: 16
cagcagggaa caacacaaga                                                    20
```

BIOMARKERS FOR ORAL TONGUE CANCER METASTASIS AND EXTRACAPSULAR SPREAD (ECS)

CROSS-REFERENCES TO RELATED APPLICATIONS

The present application claims priority to U.S. Ser. No. 60/758,432, filed Jan. 11, 2006, herein incorporated by reference in its entirety.

STATEMENT AS TO RIGHTS TO INVENTIONS MADE UNDER FEDERALLY SPONSORED RESEARCH OR DEVELOPMENT

This invention was made with Government support under NIH/NIDCR Grant No. RO1 DE15970 and NIH/NCI Grant No. CA114688. The Government has certain rights in this invention.

BACKGROUND OF THE INVENTION

Head and neck squamous cell carcinomas (HNSCCs) are a heterogeneous group of tumors that arise from the epithelium of the upper aerodigestive tract. HNSCC is the 6th most common malignancy in humans and is associated with high alcohol and tobacco use. Despite the tremendous improvements in surgery, radiotherapy and chemotherapy over the last decade, the prognosis for patients with head and neck SCC is more or less unchanged. This is because patients continue to die from metastatic disease at regional and distant sites. Improvement in patient survival requires an increased understanding of tumor metastasis so that aggressive tumors can be detected early in the disease process and targeted therapeutic interventions can be developed. Detection of local lymph node metastasis is pivotal for choosing appropriate treatment, especially for individuals diagnosed with HNSCC in the oral cavity or oropharynx (Pantel and Brakenhoff 2004). Most of these individuals have the primary tumor removed. Treatment of individuals clinically diagnosed with lymph node metastasis (N+ status) involves the additional surgical removal of a substantial portion of the neck, including all five local lymph node levels (radical neck dissection, RND). Upon histological examination of removed tissue, 10-20% of clinically diagnosed N+ individuals turn out to be metastasis-free (N0) (Woolgar 1999).

Clinical diagnosis of N0 status is even less accurate. Postoperative histological examination shows that approximately one-third of clinically diagnosed N0 individuals have metastasis-positive lymph nodes in the neck (Jones et al. 1993). Currently, there are several different strategies exist for treating diagnosed N0 individuals (Pillsbury and Clark 1997). In the "watch and wait" strategy, diagnosed N0 individuals do not undergo any neck dissection; this risks fatality by allowing overlooked metastases to spread further. Because the false-negative rate is very high, most clinics carry out neck surgery for all diagnosed N0 individuals. In these cases, a supra-myohyoid neck dissection (SOHND) is done, which removes the three upper lymph node levels (Robbins et al. 2002). SOHND is less appropriate than RND for N+ individuals falsely diagnosed as N0 and, moreover, is completely unnecessary for individuals correctly diagnosed as N0. Although SOHND is less rigorous than RND, the treatment causes disfigurement, long-term discomfort and pain and can lead to additional complications such as shoulder and neck disability (Short et al. 1984; van Wilgen et al. 2003; van Wilgen et al. 2004; van Wilgen et al. 2004). Both strategies result in inappropriate treatment because of limitations in detecting lymph node metastasis reliably.

In addition to the nodal metastasis, many studies have also suggested that extracapsular spread (ECS) of lymph node metastasis is one of the most important negative prognostic factors for several different cancer types (Mambo and Gallager 1977; Bollen et al. 1994; van der Velden et al. 1995; Yamashita et al. 1997; Ueno et al. 1998; Tachikawa et al. 1999; Lerut et al. 2003; Nakamura et al. 2005), including head and neck cancers (Johnson et al. 1981; Carter et al. 1985; Johnson et al. 1985; Snyderman et al. 1985; Hirabayashi et al. 1991; Leemans et al. 1993; Alvi and Johnson 1996; Brasilino de Carvalho 1998; Myers et al. 2001; Greenberg et al. 2003). The detection of ECS is currently done by histological examination of the dissected lymph nodes, which is also prone to the same limitations as for the current methods of nodal metastasis diagnosis. These point to the immediate needs for new diagnostic strategies.

Currently, no molecular biomarkers have been included in clinical work-up strategies for the detection of nodal metastasis and ECS. Since several genes have been reported in retrospective trials to yield prognostic information independently of the TMN classification, it is reasonable to hypothesize that molecular "fingerprints" could exist that might define sub-groups of patients with significantly more aggressive disease. The tumor cells may progress via the bloodstream or the lymphatics to colonize new areas of the body. Gene expression signatures of the primary tumor have been identified in several tumor types for increased risk of metastasis (van't Veer et al. 2002; Kikuchi et al. 2003; Ramaswamy et al. 2003; Weiss et al. 2003; Bertucci et al. 2004; Nakamura et al. 2004; Jones et al. 2005; Xi et al. 2005). The metastasis of the HNSCCs is unique in that they metastasize mainly to regional lymph nodes through the draining lymphatics, where metastasis to distant site is relatively uncommon. Several recent gene expression studies that suggested the existence of such "fingerprints" in the primary tumor for metastasis of head and neck cancer (Schmalbach et al. 2004; O'Donnell et al. 2005; Roepman et al. 2005). In this study, we carried out the genome-wide expression analysis to identify these "fingerprints" for nodal metastasis as well as ECS and further validated them using real-time quantitative RT-PCR. Transcriptional profiling capable of predicting ECS phenotype has not been reported previously.

BRIEF SUMMARY OF THE INVENTION

Generally, the methods find particular use in diagnosing or providing a prognosis for head and neck squamous cell carcinoma metastasis, by detecting RNA transcripts of molecular biomarkers with altered expression patterns in biological samples.

In one aspect, the present invention provides a method of diagnosing or providing a prognosis for head and neck squamous cell carcinoma metastasis, the method comprising the steps of: (a) contacting a biological sample comprising RNA with a reagent that specifically binds to a sequence having at least 95% identity to a marker nucleic acid selected from the group consisting of BMP2, CTTN, EEF1A1, ASAH1, MTUS1, GTSE1, MMP9, and EGFR; and (b) determining whether or not RNA representing the marker nucleic acid is overexpressed in the sample; thereby diagnosing or providing a prognosis for head and neck squamous cell carcinoma metastasis.

In another aspect, the present invention provides a method of identifying a compound that prevents or treats head and neck squamous cell carcinoma metastasis, the method comprising the steps of: (a) contacting a compound with a sample comprising a cell that overexpresses a nucleic acid selected from the group consisting of: BMP2, CTTN, EEF1A1, ASAH1, MTUS1, GTSE1, MMP9, and EGFR; and (b) determining whether or not the compound reduces expression of the nucleic acid, thereby identifying a compound that prevents or treats head and neck squamous cell carcinoma metastasis.

In another aspect, the present invention provides a method of diagnosing or providing a prognosis for extracapsular spread of a head and neck squamous cell carcinoma, the method comprising the steps of: (a) contacting a biological sample comprising RNA with a reagent that specifically binds to a sequence having at least 95% identity to a marker nucleic acid selected from the group consisting of BMP2, CTTN, EEF1A1, ASAH1, MTUS1, GTSE1, MMP9, and EGFR; and (b) determining whether or not RNA representing the marker nucleic acid is overexpressed in the sample; thereby diagnosing or providing a prognosis for extracapsular spread of a head and neck squamous cell carcinoma.

In one embodiment, the reagent is an nucleic acid probe. In another embodiment, the reagent is an oligonucleotide. In another embodiment, the reagent is an oligonucleotide array. In another embodiment, the reagent is an RT PCT primer set.

In one embodiment, the sample is from a primary cancer site. In another embodiment, the sample is from a tongue, blood, or saliva.

In one embodiment, the nucleic acid is selected from the group consisting of: BMP2, CTTN, EEF1A1, EGFR, GTSE, and MMP9. In another embodiment, the nucleic acid is CTTN or MMP9. In another embodiment, the following nucleic acids are detected: CTTN, MMP9, and EGFR, or BMP2, CTTN, GTSE, and MMP9.

In one aspect, the present invention provides a method of diagnosing or providing a prognosis for head and neck squamous cell carcinoma metastasis, the method comprising the steps of: (a) contacting a biological sample comprising protein with a reagent that specifically binds to a sequence having at least 95% identity to a marker protein selected from the group consisting of BMP2, CTTN, EEF1A1, ASAH1, MTUS1, GTSE1, MMP9, and EGFR; and (b) determining whether or not the marker protein is overexpressed in the sample; thereby diagnosing or providing a prognosis for head and neck squamous cell carcinoma metastasis.

In another aspect, the present invention provides a method of identifying a compound that prevents or treats head and neck squamous cell carcinoma metastasis, the method comprising the steps of: (a) contacting a compound with a sample comprising a cell that overexpresses a protein selected from the group consisting of: BMP2, CTTN, EEF1A1, ASAH1, MTUS1, GTSE1, MMP9, and EGFR; and (b) determining whether or not the compound reduces expression of the protein, thereby identifying a compound that prevents or treats head and neck squamous cell carcinoma metastasis.

In another aspect, the present invention provides a method of diagnosing or providing a prognosis for extracapsular spread of a head and neck squamous cell carcinoma, the method comprising the steps of: (a) contacting a biological sample comprising protein with a reagent that specifically binds to a sequence having at least 95% identity to a marker protein selected from the group consisting of BMP2, CTTN, EEF1A1, ASAH1, MTUS1, GTSE1, MMP9, and EGFR; and (b) determining whether or not the marker protein is overexpressed in the sample; thereby diagnosing or providing a prognosis for extracapsular spread of a head and neck squamous cell carcinoma.

In one embodiment, the reagent is an antibody.

In one embodiment, the sample is from a primary cancer site. In another embodiment, the sample is from a tongue, blood, or saliva.

In one embodiment, the protein is selected from the group consisting of: BMP2, CTTN, EEF1A1, EGFR, GTSE, and MMP9. In another embodiment, the protein is CTTN or MMP9. In another embodiment, the following proteins are detected: CTTN, MMP9, and EGFR, or BMP2, CTTN, GTSE, and MMP9.

BRIEF DESCRIPTION OF THE DRAWINGS

FIG. 3. Signature gene sets and Real-time quantitative RT-PCR validation of selected candidate genes. A) The signature gene sets for lymph node metastasis and ECS were generated using combination different statistical methods/different expression indices (dChip RMA and MAS5) as described in Material and Methods section. The composition of these gene set were presented with a van diagram. B) Real-time quantitative RT-PCR was performed to validate 8 selected candidate genes as described in Material and Methods section. Wilcoxon test was performed to evaluate the statistical significance of the RNA level difference among groups. The test result is also provided, as a reference. * Median value of the RNA level computed with $2^{-delta\ delta\ Ct}$ method as described previously (Livak and Schmittgen 2001), where beta-actin was used as reference gene.

DETAILED DESCRIPTION OF THE INVENTION

Introduction

Tumor metastasis is the dominant cause of death in cancer patients, including oral tongue squamous cell carcinoma (SCC) patients. However, the molecular and cellular mechanisms underlying tumor metastasis are still elusive. The identification of molecular markers associated with the metastatic process would help to understand biological mechanisms and facilitate the development of therapeutic interventions for oral tongue cancer patients. We performed global gene expression profiling on 11 lymph node metastatic (pN+) and 14 non-metastatic (pN−) SCC samples of tongue. Using stringent statistical criteria (fold difference>2, and p<0.003), a signature gene set was generated that can classify the pN+ and pN− cases with>90% accuracy.

Our expression profiling analyses also generated a second gene list that can provide superb classification power for extracapsular spread (ECS). ECS is considered as the most reliable clinical predictor of poor treatment outcomes of metastatic squamous cell carcinoma of the head and neck to regional lymph nodes. Expression profiling capable of predicting ECS phenotype has not been reported previously, so these results can be highly significant.

We validated a set of genes using real-time quantitative RT-PCR, including ASAH1, BMP2, CTTN, EEF1A1, EGFR, GTSE1, MMP-9, and MTUS1. To test the prediction/classification power of these markers, logistic model and receiver operating characteristic curve (ROC) analysis were performed based on the real-time quantitative RT-PCR results. Among the models with each individual gene, CTTN and MMP-9 show the best prediction powers (0.94 and 0.88 under curve area, respectively for pN; 0.88 and 0.95 under curve area, respectively for ECS), and the specific combination of markers in the logistic model that fit the data best, achieved a perfect specificity and sensitivity on the testing sample set. Our results demonstrated that pN and ECS can be predicted by gene expression analyses.

Definitions

The nucleic acids of Table 1 refer to nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof, (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition. Exemplary accession numbers for polypeptides and nucleic acids of the invention are as follows: BMP2: NM_001200, (SEQ ID NO:17) NP_001191 (SEQ ID NO:18) CTTN: NM_005231 (SEQ ID NO:19), NP_005222. (SEQ ID NO:20); EEF1A1: NM_001402 (SEQ ID NO:21), NP_001393 (SEQ ID NO:22); ASAH1: NM_177924 (SEQ ID NO 23), NP_808592 (SEQ ID NO:24); MTUS1: NM_001001924 (SEQ ID NO:25), NP_001001924 (SEQ ID NO:26); MMP9: NM_004994 (SEQ ID NO:27), NP_004985 (SEQ ID NO:28); GTSE1: NM_016426 (SEQ ID NO:29), NP_057510 (SEQ ID NO:30); and EGFR: NM_005228 (SEQ ID NO:31), NP_005219 (SEQ ID NO:32).

The term "cancer" refers to human cancers and carcinomas, sarcomas, adenocarcinomas, lymphomas, leukemias, solid and lymphoid cancers, etc. Examples of different types of cancer include, but are not limited to, breast cancer, gastric cancer, bladder cancer, ovarian cancer, thyroid cancer, lung cancer, prostate cancer, uterine cancer, testicular cancer, neuroblastoma, squamous cell carcinoma of the head, neck, cervix and vagina, multiple myeloma, soft tissue and osteogenic sarcoma, colorectal cancer, liver cancer (i.e., hepatocarcinoma), renal cancer (i.e., renal cell carcinoma), pleural cancer, pancreatic cancer, cervical cancer, anal cancer, bile duct cancer, gastrointestinal carcinoid tumors, esophageal cancer, gall bladder cancer, small intestine cancer, cancer of the central nervous system, skin cancer, choriocarcinoma; osteogenic sarcoma, fibrosarcoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, and acute myelocytic leukemia.

"Head and neck squamous cell carcinoma" refers to group of cancers of epithelial cell origin originating in the head and neck, including the oral cavity and pharynx. These tumors arise from diverse anatomical locations, including the oral cavity, oropharynx, hypopharynx, larynx, and nasopharynx, but in some cases can have in common an etiological association with tobacco and/or alcohol exposure. The oral cavity is defined as the area extending from the vermilion border of the lips to a plane between the junction of the hard and soft palate superiorly and the circumvallate papillae of the tongue inferiorly. This region includes the buccal mucosa, upper and lower alveolar ridges, floor of the mouth, retromolar trigone, hard palate, and anterior two thirds of the tongue. The lips are the most common site of malignancy in the oral cavity and account for 12% of all head and neck cancers, excluding nonmelanoma skin cancers. Squamous cell carcinoma is the most common histologic type, with 98% involving the lower lip. Next most common sites in order of frequency are the tongue, floor of the mouth, mandibular gingiva, buccal mucosa, hard palate, and maxillary gingiva. The pharynx consists of the oropharynx, nasopharynx, and hypopharynx. The most common sites of cancer in the oropharynx are the tonsillar fossa, soft palate, and base of tongue, followed by the pharyngeal wall. The hypopharynx is divided into the pyriform sinus (most common site of tumor involvement), posterior pharyngeal wall, and postcricoid region.

"Therapeutic treatment" and "cancer therapies" refers to chemotherapy, hormonal therapy, radiotherapy, and immunotherapy.

"Metastasis" refers to spread of a cancer from the primary tumor or origin to other tissues and parts of the body, such as the lymph nodes.

"Extracapsular" spread refers to metastasis of the cancer from the lymph nodes to other sites in the body.

"Providing a prognosis" refers to providing a prediction of the likelihood of metastasis, predictions of disease free and overall survival, the probable course and outcome of cancer therapy, or the likelihood of recovery from the cancer, in a subject.

"Diagnosis" refers to identification of a disease state, such as cancer or metastatic cancer, in a subject.

The terms "overexpress," "overexpression" or "overexpressed" interchangeably refer to a protein or nucleic acid (RNA) that is transcribed or translated at a detectably greater level, usually in a cancer cell, in comparison to a normal cell. The term includes overexpression due to transcription, post transcriptional processing, translation, post-translational processing, cellular localization (e.g., organelle, cytoplasm, nucleus, cell surface), and RNA and protein stability, as compared to a normal cell. Overexpression can be detected using conventional techniques for detecting mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a normal cell.

The terms "cancer-associated antigen" or "tumor-specific marker" or "tumor marker" interchangeably refers to a molecule (typically nucleic acid, protein, carbohydrate or lipid) that is expressed in the cell, expressed on the surface of a cancer cell or secreted by a cancer cell in comparison to a normal cell, and which is useful for the diagnosis of cancer, for providing a prognosis, and for preferential targeting of a pharmacological agent to the cancer cell. Oftentimes, a cancer-associated antigen is a molecule that is overexpressed in a cancer cell in comparison to a normal cell, for instance, 1-fold over expression, 2-fold overexpression, 3-fold overexpression or more in comparison to a normal cell. Oftentimes, a cancer-associated antigen is a molecule that is inappropriately synthesized in the cancer cell, for instance, a molecule that contains deletions, additions or mutations in comparison to the molecule expressed on a normal cell.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection such as provided on-line by the National Center for Biotechnology Information (NCBI). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of cancer antigens. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

Diagnostic and Prognostic Methods

The present invention provides methods of diagnosing or providing a prognosis for a cancer or cancer metastasis by examining protein or RNA expression of biomarkers listed in Tables 1 and 4, or a combination thereof in biological samples, including wild-type, truncated or alternatively spliced forms. Diagnosis involves determining the level of a polynucleotide or polypeptide of the invention in a patient and then comparing the level to a baseline or range. Typically, the baseline value is representative of a polynucleotide or polypeptide of the invention in a healthy person not suffering from cancer, as measured using biological sample such as a tissue sample (e.g., tongue or lymph tissue), serum, blood, or saliva. Variation of levels of a polynucleotide or polypeptide of the invention from the baseline range (either up or down) indicates that the patient has a cancer or is at risk of developing a cancer or metastatic cancer to the lymph nodes, or extracapsular spread.

PCR assays such as Taqman® allelic discrimination assay available from Applied Biosystems can be used to identify RNA. In another embodiment, mass spectroscopy can be used to detect either nucleic acid or protein. Any antibody-based technique for determining a level of expression of a protein of interest can be used. For example, immunoassays such as ELISA, Western blotting, flow cytometry, immunofluorescence, and immunohistochemistry can be used to detect protein in patient samples.

Analysis of a protein or nucleic acid can be achieved, for example, by high pressure liquid chromatography (HPLC), alone or in combination with mass spectrometry (e.g., MALDI/MS, MALDI-TOF/MS, tandem MS, etc.).

Analysis of nucleic acid can be achieved using routine techniques such as northern analysis, reverse-transcriptase polymerase chain reaction (RT-PCR), microarrays, sequence analysis, or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., Theophilus et al., and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Non-limiting examples of sequence analysis include Sanger sequencing, capillary array sequencing, thermal cycle sequencing (Sears et al., *Biotechniques*, 13:626-633 (1992)), solid-phase sequencing (Zimmerman et al., *Methods Mol. Cell. Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), and sequencing by hybridization (Chee et al., *Science*, 274:610-614 (1996); Drmanac et al., *Science*, 260:1649-1652 (1993); Drmanac et al., *Nature Biotech.*, 16:54-58 (1998)). Non-limiting examples of electrophoretic analysis include slab gel electrophoresis such as agarose or polyacrylamide gel electrophoresis, capillary electrophoresis, and denaturing gradient gel electrophoresis.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used (see, e.g., Self et al., *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)). Liposome immunoassays, such as flow-injection liposome immunoassays and liposome immunosensors, are also suitable for use in the present invention (see, e.g., Rongen et al., *J. Immunol. Methods*, 204:105-133 (1997)). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.*, 27:261-276 (1989)).

Specific immunological binding of the antibody to a protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Useful physical formats comprise surfaces having a plurality of discrete, addressable locations for the detection of a plurality of different biomarkers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more protein markers for detection at each location. Surfaces may alternatively comprise one or more discrete particles (e.g., microparticles or nanoparticles) immobilized at discrete locations of a surface, where the microparticles comprise antibodies to immobilize one or more protein markers for detection.

The analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Compositions, Kits and Integrated Systems

The invention provides compositions, kits and integrated systems for practicing the assays described herein using polynucleotides and polypeptides of the invention, antibodies specific for polypeptides or polynucleotides of the invention, etc.

The invention provides assay compositions for use in solid phase assays; such compositions can include, for example, one or more polynucleotides or polypeptides of the invention immobilized on a solid support, and a labeling reagent. In each case, the assay compositions can also include additional reagents that are desirable for hybridization. Modulators of expression or activity of polynucleotides or polypeptides of the invention can also be included in the assay compositions.

The invention also provides kits for carrying out the diagnostic assays of the invention. The kits typically include a probe that comprises an antibody or nucleic acid sequence that specifically binds to polypeptides or polynucleotides of the invention, and a label for detecting the presence of the probe. The kits may include several polynucleotide sequences encoding polypeptides of the invention.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical images.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen are sampled to obtain light intensity readings for each position. Multiple pixels are processed in parallel to increase speed. The apparatus and methods of the invention are easily used for viewing any sample, e.g., by fluorescent or dark field microscopic techniques.

EXAMPLES

The following examples are offered to illustrate, but not to limit the claimed invention.

Example 1

Biomarkers in Oral Tongue Cancer

Results

Figure 1:
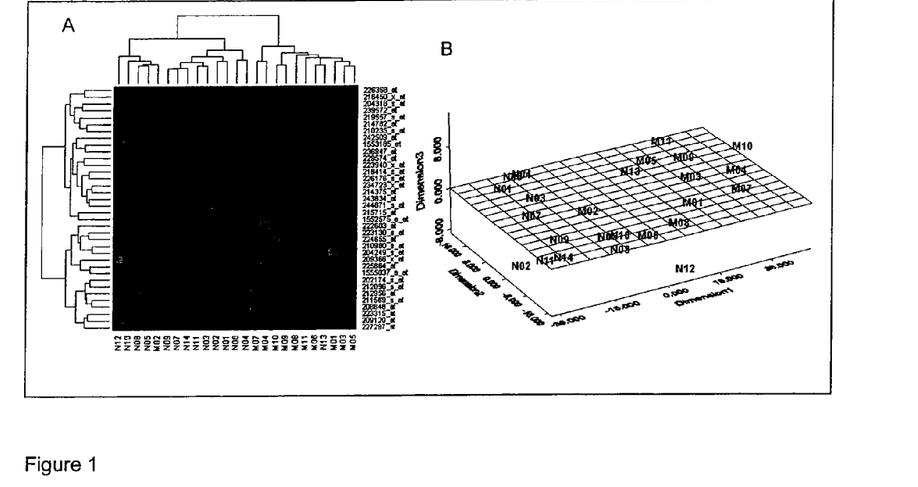
FIG. 1: Classification of metastatic tongue SCC using global gene expression analysis. Global gene expression profiling on 11 lymph node metastasis positive (pN+) and 14 lymph node metastasis negative (pN−) SCC samples of tongue was carried out using U133+2.0 array. A signature gene set of 33 genes was created based on the intersection of the significant gene lists form the 3 different expression indices that used different statistical methods (dChip, MAS5, and RMA). Hierarchical clustering (A) and MDS (multi-dimensional scaling) (B) were performed based on this signature gene set. The metastasis group (labeled with prefix M, n=11) and non-metastasis groups (labeled with prefix N, n=14).

Global gene expression profiling was performed using Affymetrix GeneChip U133+2.0 array on 11 lymph node metastatic (pN+) and 14 non-metastatic negative (pN−) OSCC samples of tongue (see Materials and Methods section). A signature gene set of 33 genes (Table 1) was created based on the intersection of the significant gene lists form the 3 different expression indices that used different statistical methods (dChip, MAS5, and RMA) that can classify the pN+ and pN− cases with >90% accuracy (FIG. 1) (The hierarchical clustering misclassified one for each of two groups).

Figure 2:
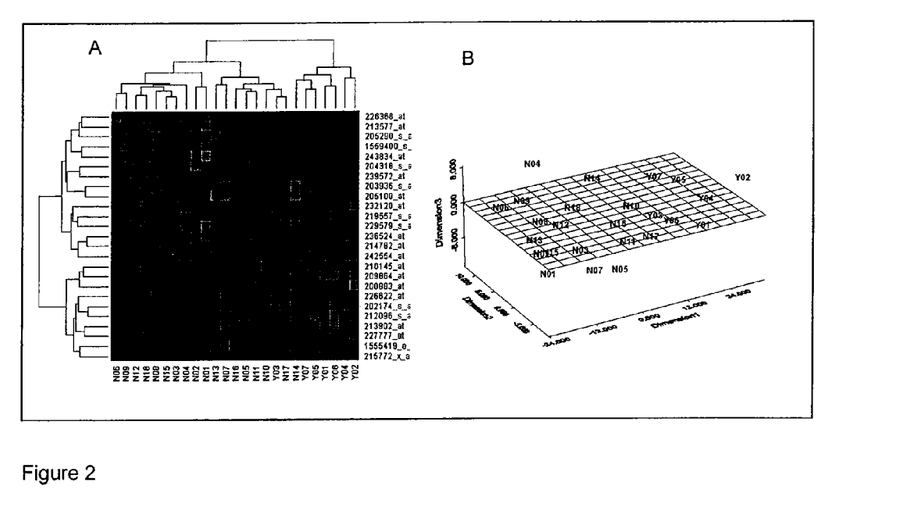
FIG. 2: classification power of the signature gene set for ECS. A second signature gene set was created for the extracapsular spread (ECS) positive (labeled with prefix Y, n=7) and ECS negative groups (labeled with prefix N, n=18). Hierarchical clustering (A) and MDS (B) were performed based on this signature gene set.

In our pN+ patient cohort, 7 of them had clinically diagnoses of extracapsular spread (ECS) positive. Our global expression profiling analyses also generated a second gene list (22 genes) that can provide superb classification power for ECS (FIGS. 2A and 2B). ECS is considered as the most reliable clinical predictor of poor treatment outcomes of metastatic squamous cell carcinoma of the head and neck to regional lymph nodes (Johnson et al. 1981; Carter et al. 1985; Johnson et al. 1985; Snyderman et al. 1985; Hirabayashi et al. 1991; Leemans et al. 1993; Alvi and Johnson 1996; Brasilino de Carvalho 1998; Myers et al. 2001; Greenberg et al. 2003). Expression profiling capable of predicting ECS phenotype has not been reported previously, so these results have high substantive significance.

Figure 3:
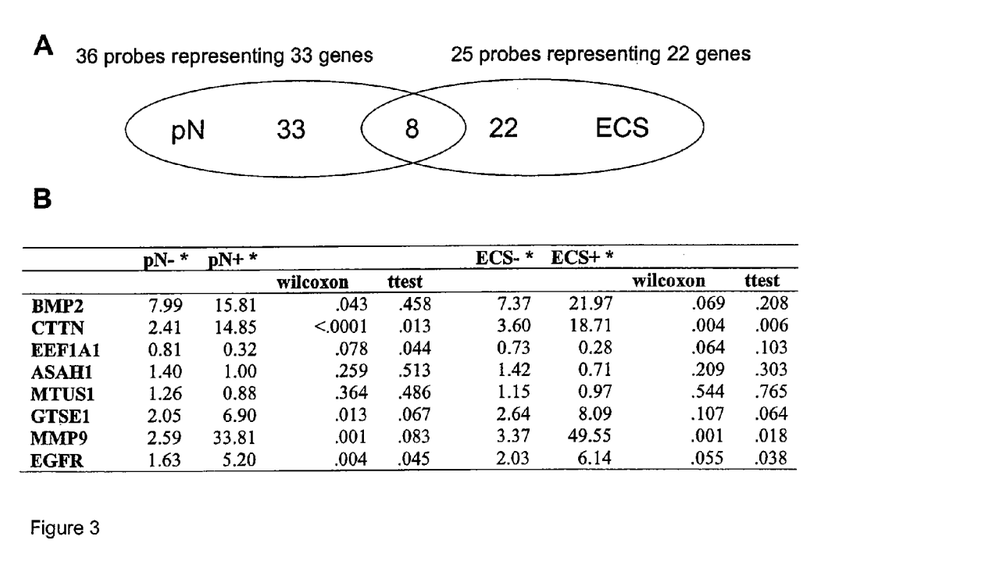

To further validate these candidate genes, real-time quantitative RT-PCR was performed to validate the expressional differences of those genes in the cases we utilized for global expression profiling study. As showed in FIG. 3B, the differences of RNA levels are either statistically significance ($p<0.05$) or suggestive ($p<0.1$) for pN− vs pN+ and ECS− vs ECS+ groups for 6 out of 8 genes tested (including BMP2, CTTN, EEF1A1, GTSE1, MMP9, EGFR).

To test the prediction/classification power of these markers, logistic model and receiver operating characteristic curve (ROC) analysis were performed based on the real-time quantitative RT-PCR results (Table 1). Among the models with each individual gene, CTTN and MMP-9 show the best prediction powers (0.94 and 0.88 under curve area, respectively for pN; 0.88 and 0.95 under curve area, respectively for ECS), and the specific combination of markers in the logistic model that fit the data best, achieved a perfect specificity and sensitivity on the testing sample set. Our results demonstrated that pN and ECS can be predicted by gene expression analyses.

5 genes (CTTN, MMP9, GTSE-1, BMP2, and EGFR) consistently overexpressed in tumors with lymph node metastasis and best predict lymph node metastasis and ECS in our models.

The prediction works better when the expression of several of the 5 genes was considered at the same time, suggesting a compounded effect of the genes in head and neck cancer progression. Our results suggest these genes may be therapeutic targets for patients with head and neck cancer. More importantly, it suggests a combination targeting several of these genes may achieve therapeutic synergy to treat or prevent tumor cell spreading and metastasis.

2) Rational of Focusing on Tongue Cancer

It has been realized that head and neck cancers are groups of diverse cancers, that developed from many different anatomical sites and associated with different risk factors (Dobrossy 2005) and genetic characteristics (Timar et al. 2005). In this study, we focused on the oral tongue cancer, the most common site for head and neck cancers.

3) Discussion of the Validated Candidate Genes

A set of candidate genes have been identified and validated in this study, including genes that known to be involved in

TABLE 1

Classification power for selected candidate genes based on real-time quantitative RT-PCR

| | Prediction power for pN−/pN+ | | | | Prediction power for ECS−/ECS+ | | | |
|---|---|---|---|---|---|---|---|---|
| | Wilcoxon (p value) | ROC (AUC) | Sensitivity | Specificity | Wilcoxon (p value) | ROC (AUC) | Sensitivity | Specificity |
| BMP2 | 0.043 | 74 | 82 | 73 | 0.069 | 74 | 86 | 68 |
| CTTN | <.0001 | 94 | 91 | 80 | 0.004 | 88 | 86 | 74 |
| EEF1A1 | 0.078 | 71 | 55 | 33 | 0.064 | 74 | 57 | 26 |
| ASAH1 | 0.259 | 64 | 27 | 73 | 0.209 | 67 | 29 | 74 |
| MTUS1 | 0.364 | 61 | 64 | 33 | 0.544 | 58 | 57 | 37 |
| GTSE1 | 0.013 | 79 | 73 | 80 | 0.107 | 71 | 71 | 74 |
| MMP9 | 0.001 | 88 | 82 | 93 | 0.001 | 95 | 100 | 89 |
| EGFR | 0.004 | 82 | 73 | 80 | 0.055 | 75 | 71 | 79 |
| | | | A Preferred Model | | | | | |
| CTTN + MMP9 + EGFR | | | 100 | 100 | CTTN + MMP9 + EGFR | | 100 | 100 |
| BMP2 + CTTN + GTSE + MMP9 | | | 100 | 100 | GTSE + MMP9 + EGFR | | 100 | 100 |

Discussion

1) Lymph Node Metastasis and Extracapsular Spread of Head and Neck Cancer

Extracapsular spread (ECS) of lymph node metastasis is one of the most important negative prognostic factors for head and neck cancers (Johnson et al. 1981; Carter et al. 1985; Johnson et al. 1985; Snyderman et al. 1985; Hirabayashi et al. 1991; Leemans et al. 1993; Alvi and Johnson 1996; Brasilino de Carvalho 1998; Myers et al. 2001; Greenberg et al. 2003). However, the underlying biology determining these aggressive features is largely unknown. Improvement in patient survival requires an increased understanding of tumor metastasis so that aggressive tumors can be detected early in the disease process and targeted therapeutic interventions can be developed. We used a global approach to uncover gene expression signatures associated with these aggressive features. Because our method covers most of human transcriptome, the differentially expressed genes consistently seen in tumors with lymph node metastasis and ECS of the node likely to be biologically important. In this study, we identified metastasis, such as MMP-9 and CTTN. MMP9 is a member of a group of secreted zinc metalloproteases which, in mammals, degrade the collagens of the extracellular matrix. The elevated expression of MMP9 has been linked to metastasis in many different cancer types (Turner et al. 2000; Osman et al. 2002). CTTN has been shown to be the oncogene resided in the 11q13 region that is found to be frequently amplified in squamous cell carcinomas of the head and neck and breast cancer (Schuuring et al. 1992; Schuuring et al. 1998). Our signature gene set also contains several candidate genes that are involved in tumorigenesis, such as BMP-2 and EGFR. BMP-2 is a member of the transforming growth factor-beta superfamily, which controls proliferation, differentiation, and other functions in many cell types. EGFR is one of the most frequently amplified and mutated gene in many different type of cancers, including head and neck SCC (Santani et al. 1991; Dassonville et al. 1993; Grandis and Tweardy 1993). Other identified candidate genes, that their roles in metastasis process have not been clearly defined, include GTSE1, EEF1A1. GTSE1 is a microtubule-localized protein. Its expression is cell cycle regulated and can induce G2/M-phase accumulation when overexpressed (Monte et al. 2000). It has been demonstrated that GTSE 1 is able to down-regulate levels and activity of the p53 tumor suppressor protein and represses its ability to induce apoptosis after DNA damage (Monte et al. 2004). EEF1A1 gene codes for the alpha subunit of elongation factor-1 which is involved in the binding of aminoacyl-tRNAs to 80S ribosomes. The involvement of this gene with the tumorigenesis is not clear.

4) Rational of Use Multiple Indices/Methods for Identification of Candidate Genes.

Several approaches have been proposed for defining a measure of expression representing the amount of the corresponding mRNA for each microarray probe set; these include the Affymetrix Microarray Analysis Suite version 5.0 (MAS 5.0) (which is now implemented in GCOS) (Affymetrix 2002), the Model Based Expression Index (MBEI) from Li and Wong (implemented in dChip) (Li and Wong 2001), the Robust Multi-array Analysis (RMA) from Irizarry et al. (2003) (Irizarry et al. 2003). Each approach utilizes a different data preparatory procedure for normalization and background correction, and its own model to define the expression index, including whether it uses only the PM intensity or both the PM and MM intensities. Consequently, the expression indices will differ when applied to the same probe set data. These differences reflect the varying biological attributes that each mathematical model highlights. Previous studies as well as our results here found the low level of overlap between the gene lists produced by the various methods and suggested that a combination of methods be used in the statistical analysis of oligonucleotide microarray data.

In this study, to narrow down candidate genes, a final gene list was compiled by selecting genes presented in at least 2 of the 3 initial gene lists generated using dChip MAS5 and RMA. The rational is that using a combination of several methods/significant gene lists will increase the statistical power to be a true biomarker and will improve reproducibility in downstream validation experiment. This process produced a gene list of 33 genes for pN+/− groups and 22 genes for ECS+/− groups. Hierarchical clustering and MDS analyses were performed on these two final gene lists and also for the original gene lists from dChip, RMA and MAS5. The results show similar pattern, which indicates that this reduction step of candidate gene list did not sacrifice the classification powers for pN and ECS.

5) Requirement for Future Validation Studies with Independent Sample Sets

Our data (ROC analyses) also demonstrated the use of these candidate genes as biomarkers for prediction/classification of lymph node metastasis and the ECS of OSCC. The specific combinations of several markers provides further enhancement of the prediction/classification power. Interestingly, combination of CTTN, MMP-9 and EGFR provide superb classification power for both pN and ECS. This suggests that same (or similar) functional/biological events account for both pN+ and ECS+ phenotypes and these phenotypes are a reflection of continuous progression of metastasis potential from pN+ to ECS+.

In summary, our results demonstrated the feasibility of utilizing biomarkers discovered by global expression profiling analyses as potential biomarkers for predict/classify OTSCC metastasis and ECS.

Materials and Methods

Tumor Procurement and RNA Extraction

Snap frozen biopsies from T4a oral tongue SCC patients were obtained with informed consent. This study is approved by Institutional Review Boards at University of California at Los Angeles and Institut Gustave-Roussy. Clinical characterizations of these patients are outlined in Table 2. The tumor stages were determined according to the American Joint Committee on Cancer (AJCC) designated classification.

Table 2

TABLE 2

Clinical Characterization of the OTSCC Patients

|  |  | pN− (n = 14) | pN+, ALL (n = 11) | pN+, ECS− (n = 4) | pN+, ECS+ (n = 7) |
| --- | --- | --- | --- | --- | --- |
| Age | Median | 54 | 65 | 55 | 66 |
|  | (Range) | 41-67 | 37-82 | 38-82 | 37-78 |
|  | Mean | 55 | 61 | 57 | 63 |
| Gender | Male (%) | 86 | 64 | 100 | 43 |
|  | Female (%) | 14 | 36 | 0 | 57 |
| Tumor Site | Tongue (%) | 100 | 100 | 100 | 100 |
| Pathological T Stage | 4 (%) | 100 | 100 | 100 | 100 |
| Pathological N Stage | 0 (%) | 100 | 0 | 0 | 0 |
|  | 1 (%) | 0 | 9 | 25 | 0 |
|  | 2 (%) | 0 | 91 | 75 | 100 |
| Pathological M Stage | 0 (%) | 93 | 100 | 100 | 100 |
|  | 1 (%) | 7 | 0 | 0 | 0 |

Cancer tissues containing more than 80% tumor cells on H&E pathological examination were selectively microdissected. The total RNA was isolated using RNeasy Mini kit (Qiagen), and quantified by the RiboGreen RNA Quantitation Reagent (Molecular Probes).

Array Hybridization and Data Analysis

A total of 150-200 ng of purified total RNA was amplified by a modified T7 RNA amplification protocol as described previously (Ohyama et al. 2000; Alevizos et al. 2001; Alevizos et al. 2002). The Enzo BioArray High Yield RNA Transcript Labeling System (Enzo) will be used for labeling the sample prior to hybridization. The biotinylated cRNA (IVT product) will be purified using the RNeasy kit (Qiagen). The quantity and purity of the biotinylated cRNA will be determined by spectrophotometry and an aliquot of sample checked by gel electrophoresis. The samples were hybridized to the Affymetrix Human Genome U133 Plus 2.0 GeneChip arrays according to the Affymetrix protocols. The arrays were scanned with a GeneChip Scanner 3000. The scanned array images were processed with GeneChip Operating software (GCOS).

The microarray data was analyzed using 3 different methods dChip, RMA and MAS5. These analysis platforms are the most commonly microarray analysis package. Using these analysis platforms, three different expression indices are evaluated and for each expression index, two widely used statistics, t-test statistic and the fold-change, were calculated for two group comparison. After screening the genes with more than 20% of present calls (provided by dChip and GCOS) over samples, three separate gene lists were generated by the stringent statistical criteria of t-test statistics and the fold-change for both pN and ECS groupings (99 and 103 transcripts were selected using dChip with the p-value <0.0033, 0.00095, and fold-change in intensity >1.9, 2.02 for pN and ECS, respectively; 99 and 98 transcripts were selected using MAS5 with the p-value <0.018, 0.015, and fold-change in intensity >2.42, 2.45 for pN and ECS, respectively; 102 and 99 transcripts were selected using RMA with the p-value<0.002, 0.002, and fold-change in log intensity>1.17, 1.16 for pN and ECS, respectively). In order to narrow down candidate genes, a final gene list was compiled by selecting genes presented in at least 2 of the 3 initial gene lists. This process produced a gene list of 33 genes for pN+/− groups and 22 genes for ECS+/− groups.

To display the consistency of the expression pattern of the signature genes, we performed the average linkage hierarchical clustering, an unsupervised method, and the multidimensional scaling (MDS). The goal of hierarchical clustering is to graphically display the similarity between genes and samples. MDS is a visualization method to project the differences in gene expression patterns among samples into multi-dimensional space and reveal the underlying structures that explain observed similarities among the samples. Hierarchical clustering and MDS analyses were performed on these two final gene lists and also for the original gene lists from dChip, RMA and MAS5. The results show similar pattern, which indicates that this reduction step of candidate gene list did not sacrifice the classification powers for pN and ECS.

Quantitative RT-PCR

The real-time quantitative RT-PCR was performed using iQ SYBR Green Supermix (Bio-Rad, Hercules, Calif.) as described previously (Li et al. 2004). All reactions were performed in triplicate. The primer sets used to test the expression of these selected candidate genes were listed in Table 3. These 8 candidate genes were chosen by their statistical significance and biological relevance. The data analysis was performed using the $2^{-delta\ delta\ Ct}$ method described previously (Livak and Schmittgen 2001), where beta-actin was used as reference gene. Both t-test and wilcoxon test were performed using S-Plus to determine the statistical significance of the expression levels for those candidate genes for pN metastasis and ECS cases.

Gene expression values based on real-time quantitative RT-PCR between two groups was compared by the nonparametric Wilcoxon test since the data is highly skewed (T-test statistics is also shown as reference). To evaluate the classification power for each gene, the Receiver Operating Characteristic (ROC) curve analysis is performed based on the logistic model with the binary outcome of pN+/− (or ECS+/−) as a dependent variable and a gene as an independent variable. The ROC curve shows the sensitivity on Y axis and (1−the specificity) on X axis for each possible cut-point of the fitted probabilities from the model. Area Under the Curve (AUC) was computed via numerical integration of the ROC curve and measure the overall diagnostic/classification power of a logistic model. Also the set of Sensitivity and Specificity is shown using the best cut-point value suggested (that minimizes the absolute value of Sensitivity minus Specificity). ROC curve analysis is also done for the logistic model with a combination of candidate genes that fit the data the most. The best fit model is found through the stepwise logistic model selection.

REFERENCES

Affymetrix (2002). "Statistical Algorithms Description Document." *Affymetrix*, Santa Clara, Calif., USA.

Alevizos, I., B. Blaeser, G. Gallagher, H. Ohyama, D. T. Wong and R. Todd (2002). "Odontogenic carcinoma: a functional genomic comparison with oral mucosal squamous cell carcinoma." *Oral Oncol* 38(5): 504-7.

Alevizos, I., M. Mahadevappa, X. Zhang, H. Ohyama, Y. Kohno, M. Posner, G. T. Gallagher, M. Varvares, D. Cohen, D. Kim, et al. (2001). "Oral cancer in vivo gene expression profiling assisted by laser capture microdissection and microarray analysis." *Oncogene* 20(43): 6196-6204.

Alvi, A. and J. T. Johnson (1996). "Extracapsular spread in the clinically negative neck (N0): implications and outcome." *Otolaryngol Head Neck Surg* 114(1): 65-70.

TABLE 3

Primer used for the real-time quantitative RT-PCR

| Gene symbol | Gene name | Affymetrix probe ID | LEFT PRIMER (SEQ ID NO:) | RIGHT PRIMER (SEQ ID NO:) |
|---|---|---|---|---|
| BMP2 | bone morphogenetic protein 2 | 205289_AT | aactctcctcctgcccctta (1) | tgcaggttcatcgtttcct (2) |
| EEF1A1 | eukaryotic translation elongation factor 1 alpha 1 | 204892_X_AT | agtctggtgatgctgccatt (3) | gcgacccaaaggtggatagt (4) |
| CTTN | Cortactin | 214782_AT | ctgagttcttccttccccact (5) | taaatgtgcaggccaaacaag (6) |
| GTSE1 | G-2 and S-phase expressed 1 | 204318_S_AT | gttctaagccgaaccaaatcc (7) | acctcagcctcccaagttcta (8) |
| ASAH1 | N-acylsphingosine amidohydrolase (acid ceramidase) 1 | 213902_AT | ttgcctcttcgtgaactttg (9) | accacccaaataccctgttg (10) |
| MMP9 | matrix metalloproteinase 9 | 203936_S_AT | gcacgacgtcttccagtacc (11) | tcaactcactccgggaactc (12) |
| EGFR | Epidermal growth factor receptor | 201983_S_AT | gcatctttaagggctccaca (13) | actatcctccgtggtcatgc (14) |
| MTUS1 | mitochondrial tumor suppressor 1 | 212096_S_AT | tatctctgctcacgcttcca (15) | cagcagggaacaacacaaga (16) |

Bertucci, F., S. Salas, S. Eysteries, V. Nasser, P. Finetti, C. Ginestier, E. Charafe-Jauffret, B. Loriod, L. Bachelart, J. Montfort, et al. (2004). "Gene expression profiling of colon cancer by DNA microarrays and correlation with histo-clinical parameters." *Oncogene* 23(7): 1377-91.

Bollen, E. C., P. H. Theunissen, C. J. van Duin, B. M. Drenth, J. A. van Noord and G. H. Blijham (1994). "Clinical significance of intranodal and extranodal growth in lymph node metastases of non-small cell lung cancer." *Scand J Thorac Cardiovasc Surg* 28(3-4): 97-102.

Brasilino de Carvalho, M. (1998). "Quantitative analysis of the extent of extracapsular invasion and its prognostic significance: a prospective study of 170 cases of carcinoma of the larynx and hypopharynx." *Head Neck* 20(1): 16-21.

Carter, R. L., L. C. Barr, C. J. O'Brien, K. C. Soo and H. J. Shaw (1985). "Transcapsular spread of metastatic squamous cell carcinoma from cervical lymph nodes." *Am J Surg* 150(4): 495-9.

Dassonville, O., J. L. Formento, M. Francoual, J. Santini, M. Schneider, F. Demard and G. Milano (1993). "Expression of epidermal growth factro receptor and survival in upper aerodigestive tract cancer." *J. Clin. Oncol.* 11: 1873-1878.

Dobrossy, L. (2005). "Epidemiology of head and neck cancer: magnitude of the problem." *Cancer Metastasis Rev* 24(1): 9-17.

Grandis, J. R. and D. J. Tweardy (1993). "Elevated levels of transforming growth factor a and epidermal growth factor receptor messenger RNA are early markers of carcinogenesis in head and neck cancer." *Cancer Research* 53: 3579-3584.

Greenberg, J. S., R. Fowler, J. Gomez, V. Mo, D. Roberts, A. K. El Naggar and J. N. Myers (2003). "Extent of extracapsular spread: a critical prognosticator in oral tongue cancer." *Cancer* 97(6): 1464-70.

Hirabayashi, H., K. Koshii, K. Uno, H. Ohgaki, Y. Nakasone, T. Fujisawa, N. Syouno, T. Hinohara and K. Hirabayashi (1991). "Extracapsular spread of squamous cell carcinoma in neck lymph nodes: prognostic factor of laryngeal cancer." *Laryngoscope* 101(5): 502-6.

Irizarry, R. A., B. M. Bolstad, F. Collin, L. M. Cope, B. Hobbs and T. P. Speed (2003). "Summaries of Affymetrix Gene-Chip probe level data." *Nucleic Acids Res* 31(4): e15.

Johnson, J. T., E. L. Barnes, E. N. Myers, V. L. Schramm, Jr., D. Borochovitz and B. A. Sigler (1981). "The extracapsular spread of tumors in cervical node metastasis." *Arch Otolaryngol* 107(12): 725-9.

Johnson, J. T., E. N. Myers, C. D. Bedetti, E. L. Barnes, V. L. Schramm, Jr. and P. B. Thearle (1985). "Cervical lymph node metastases. Incidence and implications of extracapsular carcinoma." *Arch Otolaryngol* 111(8): 534-7.

Jones, A. S., D. E. Phillips, T. R. Helliwell and N. J. Roland (1993). "Occult node metastases in head and neck squamous carcinoma." *Eur Arch Otorhinolaryngol* 250(8): 446-9.

Jones, J., H. Otu, D. Spentzos, S. Kolia, M. Inan, W. D. Beecken, C. Fellbaum, X. Gu, M. Joseph, A. J. Pantuck, et al. (2005). "Gene signatures of progression and metastasis in renal cell cancer." *Clin Cancer Res* 11(16): 5730-9.

Kikuchi, T., Y. Daigo, T. Katagiri, T. Tsunoda, K. Okada, S. Kakiuchi, H. Zembutsu, Y. Furukawa, M. Kawamura, K. Kobayashi, et al. (2003). "Expression profiles of non-small cell lung cancers on cDNA microarrays: identification of genes for prediction of lymph-node metastasis and sensitivity to anti-cancer drugs." *Oncogene* 22(14): 2192-205.

Leemans, C. R., R. Tiwari, J. J. Nauta, I. van der Waal and G. B. Snow (1993). "Regional lymph node involvement and its significance in the development of distant metastases in head and neck carcinoma." *Cancer* 71(2): 452-6.

Lerut, T., W. Coosemans, G. Decker, P. De Leyn, N. Ectors, S. Fieuws, J. Moons, P. Nafteux and D. Van Raemdonck (2003). "Extracapsular lymph node involvement is a negative prognostic factor in T3 adenocarcinoma of the distal esophagus and gastroesophageal junction." *J Thorac Cardiovasc Surg* 126(4): 1121-8.

Li, C. and W. H. Wong (2001). "Model-based analysis of oligonucleotide arrays: expression index computation and outlier detection." *Proc Natl Acad Sci USA* 98(1): 31-6.

Li, Y., M. A. St John, X. Zhou, Y. Kim, U. Sinha, R. C. Jordan, D. Eisele, E. Abemayor, D. Elashoff, N. H. Park, et al. (2004). "Salivary transcriptome diagnostics for oral cancer detection." *Clin Cancer Res* 10(24): 8442-50.

Livak, K. J. and T. D. Schmittgen (2001). "Analysis of relative gene expression data using real-time quantitative PCR and the 2(−Delta Delta C(T)) Method." *Methods* 25(4): 402-8.

Mambo, N. C. and H. S. Gallager (1977). "Carcinoma of the breast: the prognostic significance of extranodal extension of axillary disease." *Cancer* 39(5): 2280-5.

Monte, M., R. Benetti, L. Collavin, L. Marchionni, G. Del Sal and C. Schneider (2004). "hGTSE-1 expression stimulates cytoplasmic localization of p53." *J Biol Chem* 279(12): 11744-52.

Monte, M., L. Collavin, D. Lazarevic, R. Utrera, T. A. Dragani and C. Schneider (2000). "Cloning, chromosome mapping and functional characterization of a human homologue of murine gtse-1 (B99) gene." *Gene* 254(1-2): 229-36.

Myers, J. N., J. S. Greenberg, V. Mo and D. Roberts (2001). "Extracapsular spread. A significant predictor of treatment failure in patients with squamous cell carcinoma of the tongue." *Cancer* 92(12): 3030-6.

Nakamura, K., N. Ozaki, T. Yamada, T. Hata, S. Sugimoto, H. Hikino, A. Kanazawa, A. Tokuka and S, Nagaoka (2005). "Evaluation of prognostic significance in extracapsular spread of lymph node metastasis in patients with gastric cancer." *Surgery* 137(5): 511-7.

Nakamura, T., Y. Furukawa, H. Nakagawa, T. Tsunoda, H. Ohigashi, K. Murata, O. Ishikawa, K. Ohgaki, N. Kashimura, M. Miyamoto, et al. (2004). "Genome-wide cDNA microarray analysis of gene expression profiles in pancreatic cancers using populations of tumor cells and normal ductal epithelial cells selected for purity by laser microdissection." *Oncogene* 23(13): 2385-400.

O'Donnell, R. K., M. Kupferman, S. J. Wei, S. Singhal, R. Weber, B. O'Malley, Y. Cheng, M. Putt, M. Feldman, B. Ziober, et al. (2005). "Gene expression signature predicts lymphatic metastasis in squamous cell carcinoma of the oral cavity." *Oncogene* 24(7): 1244-51.

Ohyama, H., X. Zhang, Y. Kohno, I. Alevizos, M. Posner, D. T. Wong and R. Todd (2000). "Laser capture microdissection-generated target sample for high-density oligonucleotide array hybridization." *Biotechniques* 29(3): 530-6.

Osman, M., M. Tortorella, M. Londei and S. Quaratino (2002). "Expression of matrix metalloproteinases and tissue inhibitors of metalloproteinases define the migratory characteristics of human monocyte-derived dendritic cells." *Immunology* 105(1): 73-82.

Pantel, K. and R. H. Brakenhoff (2004). "Dissecting the metastatic cascade." *Nat Rev Cancer* 4(6): 448-56.

Pillsbury, H. C., 3rd and M. Clark (1997). "A rationale for therapy of the N0 neck." *Laryngoscope* 107(10): 1294-315.

Ramaswamy, S., K. N. Ross, E. S. Lander and T. R. Golub (2003). "A molecular signature of metastasis in primary solid tumors." *Nat Genet* 33(1): 49-54.

Robbins, K. T., G. Clayman, P. A. Levine, J. Medina, R. Sessions, A. Shaha, P. Som and G. T. Wolf (2002). "Neck dissection classification update: revisions proposed by the American Head and Neck Society and the American Academy of Otolaryngology-Head and Neck Surgery." *Arch Otolaryngol Head Neck Surg* 128(7): 751-8.

Roepman, P., L. F. Wessels, N. Kettelarij, P. Kemmeren, A. J. Miles, P. Lijnzaad, M. G. Tilanus, R. Koole, G. J. Hordijk, P. C. van der Vliet, et al. (2005). "An expression profile for diagnosis of lymph node metastases from primary head and neck squamous cell carcinomas." *Nat Genet* 37(2): 182-6.

Santini, J., J. L. Formento, M. Francoual, G. Milano, M. Schneider and O. Dassonville (1991). "Characterization, quantification, and potential clinical value of the epidermal growth factor receptor in head and neck squamous cell carcinomas." *Head Neck* 13: 132-139.

Schmalbach, C. E., D. B. Chepeha, T. J. Giordano, M. A. Rubin, T. N. Teknos, C. R. Bradford, G. T. Wolf, R. Kuick, D. E. Misek, D. K. Trask, et al. (2004). "Molecular profiling and the identification of genes associated with metastatic oral cavity/pharynx squamous cell carcinoma." *Arch Otolaryngol Head Neck Surg* 130(3): 295-302.

Schuuring, E., H. van Damme, E. Schuuring-Scholtes, E. Verhoeven, R. Michalides, E. Geelen, C. de Boer, H. Brok, V. van Buuren and P. Kluin (1998). "Characterization of the EMS1 gene and its product, human Cortactin." *Cell Adhes Commun* 6(2-3): 185-209.

Schuuring, E., E. Verhoeven, W. J. Mooi and R. J. Michalides (1992). "Identification and cloning of two overexpressed genes, U21B31/PRAD1 and EMS1, within the amplified chromosome 11q13 region in human carcinomas." *Oncogene* 7(2): 355-61.

Short, S. O., J. N. Kaplan, G. E. Laramore and C. W. Cummings (1984). "Shoulder pain and function after neck dissection with or without preservation of the spinal accessory nerve." *Am J Surg* 148(4): 478-82.

Snyderman, N. L., J. T. Johnson, V. L. Schramm, Jr., E. N. Myers, C. D. Bedetti and P. Thearle (1985). "Extracapsular spread of carcinoma in cervical lymph nodes. Impact upon survival in patients with carcinoma of the supraglottic larynx." *Cancer* 56(7): 1597-9.

Tachikawa, D., S. Inada, T. Kotoh, K. Futami, S. Arima and A. Iwashita (1999). "An evaluation of malignancy and prognostic factors based on mode of lymph node metastasis in esophageal carcinoma." *Surg Today* 29(11): 1131-5.

Timar, J., O. Csuka, E. Remenar, G. Repassy and M. Kasler (2005). "Progression of head and neck squamous cell cancer." *Cancer Metastasis Rev* 24(1): 107-27.

Turner, H. E., Z. Nagy, M. M. Esiri, A. L. Harris and J. A. Wass (2000). "Role of matrix metalloproteinase 9 in pituitary tumor behavior." *J Clin Endocrinol Metab* 85(8): 2931-5.

Ueno, H., H. Mochizuki and S. Tamakuma (1998). "Prognostic significance of extranodal microscopic foci discontinuous with primary lesion in rectal cancer." *Dis Colon Rectum* 41(1): 55-61.

van't Veer, L. J., H. Dai, M. J. van de Vijver, Y. D. He, A. A. Hart, M. Mao, H. L. Peterse, K. van der Kooy, M. J. Marton, A. T. Witteveen, et al. (2002). "Gene expression profiling predicts clinical outcome of breast cancer." *Nature* 415(6871): 530-6.

van der Velden, J., A. C. van Lindert, F. B. Lammes, F. J. ten Kate, D. M. Sie-Go, H. Oosting and A. P. Heintz (1995). "Extracapsular growth of lymph node metastases in squamous cell carcinoma of the vulva. The impact on recurrence and survival." *Cancer* 75(12): 2885-90.

van Wilgen, C. P., P. U. Dijkstra, J. M. Nauta, A. Vermey and J. L. Roodenburg (2003). "Shoulder pain and disability in daily life, following supraomohyoid neck dissection: a pilot study." *J Craniomaxillofac Surg* 31(3): 183-6.

van Wilgen, C. P., P. U. Dijkstra, B. F. van der Laan, J. T. Plukker and J. L. Roodenburg (2004). "Morbidity of the neck after head and neck cancer therapy." *Head Neck* 26(9): 785-91.

van Wilgen, C. P., P. U. Dijkstra, B. F. van der Laan, J. T. Plukker and J. L. Roodenburg (2004). "Shoulder and neck morbidity in quality of life after surgery for head and neck cancer." *Head Neck* 26(10): 839-44.

Weiss, M. M., E. J. Kuipers, C. Postma, A. M. Snijders, I. Siccama, D. Pinkel, J. Westerga, S. G. Meuwissen, D. G. Albertson and G. A. Meijer (2003). "Genomic profiling of gastric cancer predicts lymph node status and survival." *Oncogene* 22(12): 1872-9.

Woolgar, J. A. (1999). "Pathology of the N0 neck." *Br J Oral Maxillofac Surg* 37(3): 205-9.

Xi, L., J. Lyons-Weiler, M. C. Coello, X. Huang, W. E. Gooding, J. D. Luketich and T. E. Godfrey (2005). "Prediction of lymph node metastasis by analysis of gene expression profiles in primary lung adenocarcinomas." *Clin Cancer Res* 11(11): 4128-35.

Yamashita, H., S, Noguchi, N. Murakami, H. Kawamoto and S. Watanabe (1997). "Extracapsular invasion of lymph node metastasis is an indicator of distant metastasis and poor prognosis in patients with thyroid papillary carcinoma." *Cancer* 80(12): 2268-72.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of diagnosing, or providing a prognosis for, oral tongue squamous cell carcinoma metastasis or extracapsular spread of an oral tongue squamous cell carcinoma in a human subject having the carcinoma, the method comprising the steps of:
   (a) contacting a biological sample comprising RNA wherein the sample is from the primary cancer site of the oral tongue squamous cell carcinoma with
      i) a CTTN reagent that specifically binds to a CTTN marker nucleic acid consisting of the nucleic acid sequence of SEQ ID NO:19, wherein said contacting with the CTTN reagent is used to determine the expression level of a CTTN marker nucleic acid in the sample;
      ii) a MMP9 reagent that specifically binds to a MMP9 marker nucleic acid having the nucleic acid sequence of SEQ ID NO:27, wherein said contacting with the MMP9 reagent is used to determine the expression level of a MMP9 marker nucleic acid in the sample; and
      iii) an EGFR reagent that specifically binds to an EGFR marker nucleic acid consisting of the nucleic acid sequence of SEQ ID NO:31, wherein said contacting with the EGFR reagent is used to determine the expression level of an EGFR marker nucleic acid in the sample; and (b) determining whether or not RNA representing each of the CTTN, MMP9, and EGFR marker nucleic acids is overexpressed in the sample when compared to, respectively, RNA expression levels representing each of the CTTN, MMP9, and EGFR marker nucleic acids of a comparison population of human subjects having a tongue squamous cell carcinoma which did not metastasize; wherein the overexpression of the RNA representing each of the CTTN, MMP9, and EGFR marker nucleic acids in the sample indicates that the metastasis or extracapsular spread is present or likely to develop.

2. The method of claim 1, wherein the CTTN, MMP9 and EGFR reagents are each a nucleic acid probe.

3. The method of claim 1, wherein the CTTN, MMP9 and EGFR reagents are each an oligonucleotide.

4. The method of claim 1, wherein the CTTN, MMP9 and EGFR reagents are each a member of-an oligonucleotide array.

5. The method of claim 1, wherein the CTTN, MMP9 and EGFR reagents are each respectively a RT PCR primer set.

6. The method of claim 1, wherein a diagnosis or prognosis for the extracapsular spread of the oral tongue squamous cell carcinoma is provided.

7. The method of claim 1, wherein a diagnosis or prognosis for the metastasis of the oral tongue squamous cell carcinoma is provided.

8. A method of diagnosis, or providing a prognosis for, a tongue cell carcinoma metastasis or the extracapsular spread of an oral tongue squamous cell carcinoma in a human subject having the carcinoma, the method comprising the steps of:

(a) contacting a biological sample comprising RNA from the primary cancer site of the tongue of the subject with
i) a CTTN reagent that specifically binds to CTTN marker nucleic acid consisting of the nucleic acid sequence of SEQ ID NO:19; wherein said contacting with the CTTN reagent is used to determine the expression level of a CTTN marker nucleic acid in the sample;
ii) a MMP9 reagent that specifically binds to a MMP9 marker nucleic acid consisting of the nucleic acid sequence of SEQ ID NO:27; wherein said contacting with the MMP9 reagent is used to determine the expression level of a MMP9 marker nucleic acid in the sample;
iii) a BMP2 reagent that specifically binds to a BMP2 marker nucleic acid consisting of the nucleic acid seciuence of SEQ ID NO:17; wherein said contacting with the BMP2 reagent is used to determine the expression level of a BMP2 marker nucleic acid in the sample;
iv) a GTSE1 reagent that specifically binds-to a GTSE1 marker nucleic acid consisting of the nucleic acid sequence of SEQ ID NO:29; wherein said contacting with the GTSE1 reagent is used to determine the expression level of a GTSE1 marker nucleic acid in the sample; and b) comparing the expression levels determined for the CTTN, BMP2, and GTSE1 marker nucleic acids to, respectively, the CTTN, MMP9, BMP2, and GTSE1 marker nucleic acid expression levels of a comparison population of human subjects having a tongue squamous cell carcinoma which did not metastasize; wherein a determination that each of the CTTN, MMP9, BMP2, and GTSE1 marker nucleic acids is overexpressed relative to the comparison population indicates that the metastasis or the extracapsular spread is present or likely to develop.

9. The method of claim 8, wherein the CTTN, MMP9, BMP2, and GTSE1 reagents are each a nucleic acid probe.

10. The method of claim 8, wherein the CTTN, MMP9, BMP2, and GTSE1 reagents are each an oligonucleotide.

11. The method of claim 8, wherein the CTTN, MMP9, BMP2, and GTSE1 reagents are each members of an oligonucleotide array.

12. The method of claim 8, wherein the CTTN, MMP9, BMP2, and GTSE1 reagents are each respectively a RT PCR primer set.

* * * * *